US008563053B2

(12) United States Patent
Mousa et al.

(10) Patent No.: US 8,563,053 B2
(45) Date of Patent: Oct. 22, 2013

(54) COMPOSITIONS AND METHODS OF NATURAL PRODUCTS IN NANOFORMULATIONS FOR THE PREVENTION AND TREATMENT OF OSTEOPOROSIS

(76) Inventors: Shaker A. Mousa, Wynantskill, NY (US); Mohammed H. Qari, Jeddah (SA); Mohammed S. Ardawi, Jeddah (SA)

(*) Notice: Subject to any disclaimer, the term of this patent is extended or adjusted under 35 U.S.C. 154(b) by 215 days.

(21) Appl. No.: 12/912,826

(22) Filed: Oct. 27, 2010

(65) Prior Publication Data

US 2011/0104283 A1    May 5, 2011

Related U.S. Application Data

(60) Provisional application No. 61/279,962, filed on Oct. 29, 2009.

(51) Int. Cl.
| | |
|---|---|
| A61K 36/31 | (2006.01) |
| A61K 8/18 | (2006.01) |
| A61K 8/97 | (2006.01) |
| A61K 9/14 | (2006.01) |
| A61K 31/045 | (2006.01) |
| A61K 31/59 | (2006.01) |
| A61K 31/70 | (2006.01) |
| A61K 33/06 | (2006.01) |
| A61K 33/14 | (2006.01) |
| A61K 33/32 | (2006.01) |
| A61K 36/00 | (2006.01) |

(52) U.S. Cl.
USPC ............... 424/755; 424/49; 424/58; 424/489; 424/639; 424/675; 424/678; 424/681; 424/682; 424/696; 424/777; 514/23; 514/25; 514/27; 514/28; 514/167; 514/168; 514/729

(58) Field of Classification Search
USPC ........................................................ 424/755
See application file for complete search history.

(56) References Cited

U.S. PATENT DOCUMENTS

| | | | | |
|---|---|---|---|---|
| 3,224,942 | A | * 12/1965 | Martin | ........................ 424/94.65 |
| 8,178,013 | B2 | 5/2012 | Kim | |
| 2004/0072765 | A1 * | 4/2004 | Kelly et al. | ...................... 514/27 |
| 2005/0053668 | A1 | 3/2005 | Vail | |
| 2007/0053987 | A1 | 3/2007 | Bayer et al. | |
| 2007/0237827 | A1 | 10/2007 | Sung et al. | |

FOREIGN PATENT DOCUMENTS

| | | | |
|---|---|---|---|
| JP | 11-012192 | A * | 1/1999 |
| WO | WO 2007/086651 | A1 * | 8/2007 |

OTHER PUBLICATIONS

Abdullah bin Habeeballah bin Abdullah Juma, "The Effects of *Lepidium sativum* Seeds on Fracture-Induced Healing in Rabbits", MedGenMed. 2007; 9(2): 23 (13 pages).*
S. K. Ahsan, M. Tariq, M. Ageel, M. A. ALYAHYAand A. H. Shah, "Studies on Some Herbal Drugs Used in Fracture Healing", International Journal of Crude Drug Research, 27 (1989), No. 4, pp. 235-239.*
Sheel Sharma and Nidhi Agarwal, "Nourishing and healing prowess of garden cress (*Lepidium sativum* Linn.)—A review", Indian Journal of Natural Products and Resources, 2(3), 2011, 292-297.*
S.O. Bafeel and S.S. Ali, "The Potential Liver Toxicity of *Lepidium sativum* Seeds in Albino Rats", Research Journal of Biological Sciences, 4(12): 1250-1258, 2009.*
Lingjie Fu, Tingting Tang, Yanying Miao, Yongqiang Hao and Kerong Dai, "Effect of 1,25-dihydroxy vitamin D3 on fracture healing and bone remodeling in ovariectomized rat femora", Bone 44 (2009) 893-898.*
Peter F. Brumbaugh, Donald P. Speer and Michael J. Pitt, "A Metabolite of Vitamin D That Promotes Bone Repair", American Journal of Pathology, 1982, 106:171-179.*
Sha Jin and Kaiming Ye, "Nanoparticle-Mediated Drug Delivery and Gene Therapy", Biotechnology Progress 2007, 23, 32-41.*
Chen-Guang Liu, Kashappa Goud H. Desai, Xi-Guang Chen and Hyun-Jin Park, "Linolenic Acid-Modified Chitosan for Formation of Self-Assembled Nanoparticles", Journal of Agricultural and Food Chemistry 2005, 53, 437-441.*
T. P. Dew, A. J. Day and M. R. A. Morgan, "Bone mineral density, polyphenols and caffeine: a reassessment", Nutrition Research Reviews (2007), 20, 89-105.*
Sophie E. Putnam, Andy M. Scutt, Katrina Bicknell, Caroline M. Priestley and Elizabeth M. Williamson, "Natural Products as Alternative Treatments for Metabolic Bone Disorders and for Maintenance of Bone Health", Phytotherapy Research 21, 99-112 (2007).*
M. Prabaharan and J. F. Mano, "Chitosan-Based Particles as Controlled Drug Delivery Systems", Drug Delivery, 12:41-57, 2005.*
Mehrdad Hamidi, Amir Azadi and Pedram Rafiei, "Hydrogel nanoparticles in drug delivery", Advanced Drug Delivery Reviews 60 (2008) 1638-1649.*
Beom-Su Kim, Cheol-Sang Kim and Kang-Min Lee, "The Intracellular Uptake Ability of Chitosan-coated Poly (D,L-lactideco—glycolide) Nanoparticles", Archives of Pharmaceutical Research vol. 31, No. 8, 1050-1054, 2008.*

(Continued)

*Primary Examiner* — John Pak
*Assistant Examiner* — Nathan W Schlientz
(74) *Attorney, Agent, or Firm* — Schmeiser, Olsen & Watts, LLP

(57) ABSTRACT

A composition and method for treating a bone condition of an animal. The composition includes a nanoformulation of active ingredients. The active ingredients include *Lepidium Sativum* or other *Lepidium* extracts, calcium, vitamin D, and antioxidants. The method for treating a bone condition includes introducing the composition into the animal.

22 Claims, No Drawings

(56) References Cited

OTHER PUBLICATIONS

Whitney & Rolfes, Understanding Nutrition. Ninth edition, 2002, Wadsworth Group; Vitamin D, Chapter 11; pp. 363-368.
Assessment of Fracture Risk and Its Application to Screening for Postmenopausal Osteoporosis; Report of a WHO Study Group. World Health Organization Technical Report Series, Geneva 1994; 843; pp. 1-129.
Mayes, Stacey, L; Review of Postmenopausal Osteoporosis Pharmacotherapy; Nutrition in Clinical Practice; Jun. 2007: 22; pp. 276-285.
Who Are Candidates for Prevention and Treatment for Osteoporosis? Osteoporosis International (1997) 7; pp. 1-6.
Cashman, Kevin D.; Diet, Nutrition and Bone Health. The Journal of Nutrition; Nov 2007; 137, 11S; Research Library; Supplement; pp. 2507S-2512S.
National Osteoporosis Foundation. America's Bone Health: The State of Osteoporosis and Low Bone Mass in Our Nation; Washington DC: National Osteoporosis Foundation; 2002. G-830; 16 pages.
Cooper et al.; Population-Based Study of Survival after Osteoporotic Fractures; American Journal of Epidemiology; 1993; vol. 137, No. 9; pp. 1001-1005.
Leibson et al.; Mortality, Disability, and Nursing Home Use for Persons with and without Hip Fracture: A Population-Based Study; 2002 by the American Geriatrics Society; JAGS 50; pp. 1644-1650.
Magaziner et al.; Excess Mortality Attributable to Hip Fracture in White Women Aged 70 Years and Older; American Journal of Public Health, Oct. 1997, vol. 87, No. 10; pp. 1630-1636.
Magaziner et al.; Predictors of Functional Recovery One Year Following Hospital Discharge for Hip Fracture: A Prospective Study; Journal of Gerontology:Medical Sciences, May 1990, vol. 45, No. 3; pp. M101-M107.
Riggs et al.; The Worldwide Problem of Osteoporosis: Insights Afforded by Epidemiology; Bone, vol. 17, No. 5 Supplement; Nov. 1995; pp. 505S-511S.
Kannus et al.; Epidemiology of Osteoporotic Ankle Fractures in Elderly Persons in Finland; Dec. 15, 1996 Annals of Internal Medicine; vol. 125, No. 12; pp. 975-978.
Gullberg et al.; World-wide Projections for Hip Fracture; Osteoporos Int (1997) 7; pp. 407-413.
Cooper et al.; Hip Fractures in the Elderly: A World-Wide Projection; Osteoporos Int (1992), 2; pp. 285-289.
Ahmadi-Abhari et al.; Burden of Hip Fracture in Iran; Calcified Tissue International (2007) 80; pp. 147-153.
Lau, Edith M. C.; Epidemiology of Osteoporosis; Best Practice & Research Clinical Rheumatology (2001), vol. 15, No. 3; pp. 335-344.
Osteoporosis Society of India (Feb. 10, 2003) Action Plan Osteoporosis; Consensus statement of an expert group; New Delhi; pp. 1-34.
Shatrugna et al.; Bone status of Indian women from a low-income group and its relationship to the nutritional status. Osteoporos Int (2005) 16; pp. 1827-1835.
Rowe et al.; An Epidemiological Study of Hip Fracture—A Comparison Between 1991 and 2001. Korean Journal of Bone Metabolism (2003) 10; pp. 109-120.
Ghannam et al.; Bone Mineral Density of the Spine and Femur in Healthy Saudi Females: Relation to Vitamin D Status, Pregnancy, and Lactation; Calcified Tissue International (Jul. 1999) 65; pp. 23-28.
Bubshait et al.; Economic Implications of Osteoporosis-Related Femoral Fractures in Saudi Arabian Society; Calcified Tissue International (2007) 81; pp. 455-458.
Sadat-Ali et al.; Effect of parity on bone mineral density among postmenopausal Saudi Arabian women; Saudi Med J 2005; vol. 26 (10); pp. 1588-1590.
El-Desouki, Mahmoud; Bone Mineral Density of the Spine and Femur in the Normal Saudi Population; Saudi Medical Journal 1995; 16(1): pp. 30-35.
Sadat-Ali et al.; Osteoporosis among male Saudi Arabs: a pilot study; Ann Saudi Med 26(6) Nov.-Dec. 2006; pp. 450-454.
El-Desouki et al.; High prevalence of osteoporosis in Saudi men; Saudi Medical Journal 2007; vol. 28, No. 5; pp. 774-777.
International Osteoporosis Foundation, Facts and statistics about osteoporosis and its impact. [online]. 9 pages. [retrieved on May 5, 2008]. Retrieved from the Internet: <URL: http://www.iofbonehealth.org/facts-and-statistics.html>.
Akkas et al.; Effect of Medication on Biomechanical Properties of Rabbit Bones: Heparin Induced Osteoporosis; Clinical Rheumatology, 1997, vol. 16, No. 6; pp. 585-595.
Bellingham et al.; Bisphosphonate (Pamidronate/APD) Prevents Arthritis-Induced Loss of Fracture Toughness in the Rabbit Femoral Diaphysis; Journal of Orthopaedic Research (1995); vol. 13, No. 6; pp. 876-880.
Huang et al.; Osteoblastic Differentiation of Rabbit Mesenchymal Stem Cells Loaded in a Carrier System of Pluronic F127 and Interpore; Chang Gung Med J. vol. 29, No. 4 Jul.-Aug. 2006; pp. 363-372.
Ketchen et al.; The biological effects of magnetic fields on man; American Industrial Hygiene Association Journal 1978 (39); pp. 1-11.
Cook et al.; The Otto Aufranc Award; Strut Allograft Healing to the Femur—With Recombinant Human Osteogenic Protein-1; Clinical Orthopaedics and Related Research 2000, No. 381; pp. 47-57.
Ripamonti, U.; Bone induction by recombinant human osteogenic protein-1 (hOP-1, BMP-7) in the primate Papio ursinus with expression of mRNA of gene products of the TGF-beta superfamily; Journal of Cellular and Molecular Medicine, 2005, vol. 9, No. 4; pp. 911-928.
Deibert et al.; Ion Resonance Electromagnetic Field Stimulation of Fracture Healing in Rabbits with a Fibular Osteotomy; Journal of Orthopaedic Research (1994) vol. 12, No. 6; pp. 878-885.
Bruce et al.; Effect of a Static Magnetic Field on Fracture Healing in a Rabbit Radius; Preliminary Results; Clinical Orthopaedics and Related Research, Sep. 1987; No. 222: pp. 300-305.
Bharali et al.; Cross-linked polyvinylpyrrolidone nanoparticles: a potential carrier for hydrophilic drugs; Journal of Colloid and Interface Science 258 (2003); pp. 415-423.
Kumar et al.; Efficacy of Lytic Peptide-Bound Magnetite Nanoparticles in Destroying Breast Cancer Cells; Journal of Nanoscience and Nanotechnology 2004, vol. 4, No. 3; pp. 245-249.
U.S. Appl. No. 12/912,853, filed Oct. 27, 2010, Confirmation No. 2819.
U.S. Appl. No. 12/912,902, filed Oct. 27, 2010, Confirmation No. 2889.
Final Office Action (Mail Date Oct. 31, 2012) for U.S. Appl. No. 12/912,902, filed Oct. 27, 2010; Confirmation No. 2889.
Office Action (Mail Date Oct. 9, 2012) for U.S. Appl. No. 12/912,853; filed Oct. 27, 2010; Confirmation No. 2819.
N Nafee, S Taetz, M Schneider, UF Schaefer, C-M Lehr. "Chitosan-coated PLGA nanoparticles for DNA/RNA delivery: effect of the formulation parameters on complexation and transfection of antisense oligonucleotides. Nanomedicine: Nanotechnology, Biology, and Medicine." vol. 3, 2007, pp. 173-183.
Yamada et al.; "Bone Regeneration Following Injection of Mesenchymal Stem Cells and Fibrin Glue with a Biodegradable Scaffold"; Journal of Cranio-Maxillofacial Surgery; vol. 31; 2003; pp. 27-33.
Leach et al.; "Bone Engineering by Controlled Delivery of Osteoinductive Molecules and Cells"; Expert Opin. Biol. Ther.; (2004) 4(7): 1015-1027.

* cited by examiner

COMPOSITIONS AND METHODS OF NATURAL PRODUCTS IN NANOFORMULATIONS FOR THE PREVENTION AND TREATMENT OF OSTEOPOROSIS

CROSS-REFERENCES TO RELATED APPLICATIONS

This patent application claims priority to U.S. Provisional No. 61/279,962, filed on Oct. 29, 2009, which is incorporated herein by reference in its entirety.

FIELD OF THE INVENTION

This invention pertains to methods and compositions for prevention and/or treatment of a bone condition such as osteoporosis and bone fracture.

BACKGROUND OF THE INVENTION

Fracture healing and its pathophysiological process have been the axis of enormous studies and observations. Factors accelerating or hindering healing were diverse and unpredictable (Ketchen E E, Porter W E, Bolton N E, The biological effects of magnetic fields on man, Am Ind Hyg Assoc J. 1978; 39:1). Examples were the utilization of recombinant osteogenic protein-1, which accelerates fracture healing (Cook S D, Barrack R L, Santman M, Patron L P, Salkeld S L, Whitecloud T S., The Otto Aufranc Award, Strut allograft healing to the femur with recombinant human osteogenic protein-1, Clin Orthop Relat Res. 2000; 381:47-57, Abstract; Ripamonti U. Bone induction by recombinant human osteogenic protein-1 (hOP-1, BMP-7) in the primate Papio ursinus with expression of mRNA of gene products of the TGF-beta superfamily, J Cell Mol Med. 2005; 9:911-928. Abstract), mechanical vibration along the axis of the fracture (Han Z B, Chen L P, Yang X Z. Experimental study of fracture healing promotion with mechanical vibration in rabbits [in Chinese], Chung Hua Wai Ko Tsa Chih. 1994; 32:215-216, Abstract), ion resonance electromagnetic field stimulation (Diebert M C, McLeod B R, Smith S D, Liboff A R, Ion resonance electromagnetic field stimulation of fracture healing in rabbits with a fibular osteotomy. J Orthop Res. 1994; 12:878-885. Abstract), and static magnetic force with samarian cobalt magnets (Bruce G K, Howlett C R, Huckstep R L., Effect of a static magnetic field on fracture healing in a rabbit radius preliminary result, Clin Orthop Related Res. 1987; 222:300-305).

Osteoporosis is one of the critical diseases with which the aging population is faced, along with heart disease, stroke, diabetes, and cancer. Osteoporosis affects many women as they get older with the risk of bone fractures becoming a common reality. In a Canadian review, researchers discovered 45 natural products claiming to be of benefit, of which 15 had some evidence of effectiveness. Only 3 products, phytoestrogens, dehydroepiandrosterone (DHEA) and vitamin K2, were found to have reliable evidence (although still limited) they were useful in treating osteoporosis. Since hormone replacement therapy (HRT) for osteoporosis has diverse and sometimes untoward effects, alternative methods have been sought from among natural products. Using an ovariectomized (OVX) rat model along with a bone tissue culture model, several kinds of natural products (e.g. traditional herbal formulae, herbal medicines, food components, isoflavone, and polyphenols) have been found to be effective as estradiol in preventing the development of bone loss by various mechanisms.

However, other products and therapies are needed for preventing osteoporosis generally, and postmenopausal osteoporosis specifically.

SUMMARY OF THE INVENTION

The present invention provides a composition, comprising a nanoformulation of active ingredients, wherein said active ingredients comprise *Lepidium Sativum* or other *Lepidium* extracts, calcium, vitamin D (e.g., vitamin D2/vitamin D3), and antioxidants.

The present invention provides a method for treating a bone condition of an animal, said method comprising: treating the bone condition of the animal, said treating comprising introducing the composition of the present invention into the animal.

DETAILED DESCRIPTION OF THE INVENTION

The present invention provides nano-natural and natural products in a composition used for the prevention and treatment of a bone condition in an animal (e.g., osteoporosis and/orbone fracture). The composition of the present invention may include natural supplements in osteoporosis and bone repair disorders.

In one embodiment, nanoformulations of the present invention include nanoparticles such as, inter alia, PLGA nanoparticles, chitosan nanoparticles, or chitosan cross linked to fatty/bile acids nanoparticles.

In one embodiment, the active ingredients of a composition of the present invention are in a nanoformulation that includes: *Lepidium Sativum* or other *Lepidium* extracts or isolated/synthesized active ingredients, calcium, vitamin D (e.g., vitamin D2/_vitamin D3), and at least one antioxidants such as lycopene, green tea extract, pomegranate extract and flavonoids or their combinations. In one embodiment, the active ingredients may be encapsulated within the nanoparticles. In one embodiment, the active ingredients may additionally include: bromelain plus calcium/magnesium (2/1 ratio), manganese, and vitamin D to be encapsulated in natural nanoformulations for optimal oral delivery. In one embodiment, the at least one antioxidant is selected from the group consisting of naturally driven or synthesized flavonoids/isoflavones, lycopene, green tea extract and/or its ingredients, pomegranate extract and/or its ingredients, and combinations thereof.

In one embodiment, routes of administration for introducing the composition into an animal (e.g., a human being or a non-human species of animal) include: oral, topical, injectable, toothpaste delivery.

The composition may be administered in any desired and effective manner: as compositions for oral ingestion, or for parenteral or other administration in any appropriate manner such as intraperitoneal, subcutaneous, intratumoral, topical, intradermal, inhalation, intranasal, rectal, vaginal, sublingual, intramuscular, intravenous, intra-arterial, intrathecal, or intralymphatic. Regardless of the route of administration selected, the composition may be formulated into pharmaceutically-acceptable dosage forms by conventional methods known to those of ordinary skill in the art (e.g., see: *Remington's Pharmaceutical Sciences*, Mack Publishing Co., Easton, Pa.). Pharmaceutical carriers are well known in the art (e.g., see: *Remington's Pharmaceutical Sciences* cited above and *The National Formulary*, American Pharmaceutical Association, Washington, D.C.) and include sugars (e.g., lactose, sucrose, mannitol, and sorbitol), starches, cellulose preparations, calcium phosphates (e.g., dicalcium phosphate, tricalcium phosphate and calcium hydrogenphosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and triglycerides), biodegradable polymers (e.g., polylactide-polyglycolide, poly[orthoesters], and poly[anhydrides]), elastomeric matrices, liposomes, microspheres, oils (e.g., corn, germ, olive, castor, sesame, cottonseed, and groundnut), cocoa butter, waxes, paraffins, silicones, talc, silicylate, and the like.

Suitable carriers used included in the composition of the present invention should be compatible with the other ingredients of the composition. Carriers suitable for a selected dosage form and intended route of administration are well known in the art, and acceptable carriers for a chosen composition, dosage form and method of administration can be determined using ordinary skill in the art.

The composition of the present invention may, optionally, contain one or more additional agents commonly used in pharmaceutical compositions. These agents are well known in the art and include but are not limited to (1) fillers or extenders, such as starches, lactose, sucrose, glucose, mannitol, silicic acid or the like; (2) binders, such as carboxymethylcellulose, alginates, gelatin, polyvinyl pyrrolidone, hydroxypropylmethyl cellulose, sucrose, acacia or the like; (3) humectants, such as glycerol or the like; (4) disintegrating agents, such as agar-agar, calcium carbonate, potato or tapioca starch, alginic acid, certain silicates, sodium starch glycolate, cross-linked sodium carboxymethyl cellulose, sodium carbonate or the like; (5) solution retarding agents, such as paraffin or the like; (6) absorption accelerators, such as quaternary ammonium compounds or the like; (7) wetting agents, such as acetyl alcohol, glycerol monostearate or the like; (8) absorbents, such as kaolin, bentonite clay or the like; (9) lubricants, such as talc, calcium stearate, magnesium stearate, solid polyethylene glycols, sodium lauryl sulfate or the like; (10) suspending agents, such as ethoxylated isostearyl alcohols, polyoxyethylene sorbitol and sorbitan esters, microcrystalline cellulose, aluminum metahydroxide, bentonite, agar-agar, tragacanth or the like; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, polyamide powder or the like; (13) inert diluents, such as water, other solvents or the like; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, waxes or the like; (18) opacifying agents; (19) adjuvants; (20) emulsifying and suspending agents; (21), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols, fatty acid esters of sorbitan or the like; (22) propellants, such as chlorofluorohydrocarbons or the like and volatile unsubstituted hydrocarbons, such as butane, propane or the like; (23) antioxidants; (24) agents which render the formulation isotonic with the blood of the intended recipient, such as sugars, sodium chloride or the like; (25) thickening agents; (26) coating materials, such as lecithin or the like; and (27) sweetening, flavoring, coloring, perfuming and preservative agents. Each such ingredient or material should be compatible with the other ingredients of the formulation. Agents suitable for a selected dosage form and intended route of administration are well known in the art, and acceptable ingredients and materials, dosage form and method of administration may be readily determined by those of ordinary skill in the art.

A composition in accordance with the present invention that are suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations can be prepared by methods well known in the art.

EXAMPLES

Example 1

Synthesis of Alginate-Chitosan Nanoparticles

Alginate-chitosan nanoparticles encapsulating natural product driven active ingredients will be synthesized using the ionic gelation method. Low viscosity sodium alginate and low molecular weight chitosan will be used for the synthesis of the nanoparticles. The alginate solution will be prepared in deionized water, The chitosan solution will be prepared in 1% v/v acetic acid. The pH of both solutions will be adjusted to approximately 6.0, and the solutions will be filtered (0.22 μm pore size) prior to use. Nanoparticles will be prepared under sterile conditions by mixing appropriate volumes of 0.005% (w/w) sodium alginate and primary active ingredient, followed by the addition of 1% (w/w) chitosan under stiffing for 2 hours (hrs) at room temperature. The amount of natural product driven active ingredients will be adjusted until maximum loading efficiency is achieved. Nanoparticles will be characterized by DLS, zeta size and TEM. For co-encapsulation of two or more natural product driven active ingredients, an appropriate amount of the main ingredient will added to the solution along with other secondary active ingredients.

Example 2

Synthesis of Hybrid Cross Linked Polyvinylpyrrolidone (PVP) Hydrogel Nanoparticles Hybrid crosslinked PVP hydrogel nanoparticles will be synthesized using a modification of the method described by Bharali et al (2003). Nanoparticles encapsulating natural product driven active ingredients will be synthesized by in situ polymerization of various monomers, as described below. Polymerization reactions will be carried in a reverse micellar environment. Sodium bisethylhexylsulphosuccinate or aerosol OT (AOT; Sigma Alidrich, St. Louis, Mo., USA) will be used as a surfactant for micelle formation. Surfactant (either sodium bisethylhexylsulphosuccinate or AOT) will be dissolved in n-hexane (typically 0.03M to 0.1M AOT in hexane). Aqueous solutions of monomer will be added together with the cross-linking reagent N N' methylenebisacrylamide (MBA), the initiator ammonium persulphate (APS), the activator ferrous ammonium sulphate (FAS), and where indicated, an aqueous solution of natural active ingredient (s). The polymerization reaction will be carried out in the presence of $N_2$ gas. The monomers to be tested are vinylpyrrolidone (VP), N-isopropylacrylamide (NIPAAM) and N-3 aminopropylmethylacrylamide (APAAM). For co-encapsulation of two or more natural product driven active ingredients, an appropriate amount of the main ingredient will added to the solution along with other secondary active ingredients to the reverse micelles. To initiate the polymerization reaction, 15 µl of a saturated solution of APS (2% w/w of monomers) and 20 µl of a 0.05% w/v solution FAS (0.07% w/w of monomers) will be used. The reaction will be allowed to proceed at room temperature for 2-3 hrs.

A typical experiment is as follows. In 40 ml of 0.03 M AOT in hexane, there will be added 63 µl of freshly distilled VP, 30 µl APAAM and 200 µl of NIPAAM in water (200 mg/ml each), 50 µl of MBA (0.5 mg/ml), 10 µl of 1% FAS and 100 µl of aqueous of two or more natural product driven active ingredients. An appropriate amount of the main ingredient will added to the solution along with other secondary active ingredients. The reaction solution will be purged with $N_2$ gas for 30 minutes, and 15 µl of a saturated solution of APS will be added. Polymerization will be carried out in the presence of $N_2$ gas at room temperature for 2-3 hrs with continuous stirring. Nanoparticles of random copolymers of VP-NIPAAM-APAAM will form in the aqueous core of the reverse micellar system. The nanoparticles will remain dispersed in the organic solvent, and be separated out by the addition of 10 mL of ethanol, followed by centrifugation at 10,000×g. The nanoparticles will be repeatedly washed with ethanol at least 3-4 times and redispersed in sterile deionized water.

Example 3

Synthesis of Chitosan Grafted PLGA Nanoparticles

Chitosan grafted PLGA nanoparticles will be prepared by a modification of a method originally described by Kumar et al (2004). In brief, this double emulsion-diffusion-evaporation technique of synthesis of nanoparticles is as follows: 50 mg of PLGA will be dissolved in 2 mL of ethyl acetate, and then 200 µl of a solution of primary active ingredient will be added. The mixture will be sonicated for 5 seconds using a probe sonicator, and then the emulsion will immediately be added to an aqueous stabilizer mixture, containing 100 mg of polyvinyl alcohol (PVA) and 10 mg of chitosan in 10 ml of water, dropwise with stirring. The entire solution will be sonicated again for approximately 10 seconds using a probe sonicator. The emulsion will be stirred at room temperature for 1 hr, and then the organic phase will be removed using a rotatory evaporator. For co-encapsulation of primary ingredient, an appropriate amount will added along with the secondary ingredient during the synthesis step.

Example 4

Entrapment Efficiency

Entrapment efficiency for of two or more natural product driven active ingredients will be determined by filtering a known amount of the nanoparticles through a 0.1 µm filter membrane to separate free natural ingredients listed in the application. The amount of active ingredient will is determined using high performance liquid chromatography (HPLC). Entrapment efficiency (E %) will be determined based on the total concentration of drug (primary or secondary ingredient) in the system (free+encapsulated; $[Drug]_0$) and the concentration of drug in the filtrate ($[Drug]_f$) using the following formula:

$$E\% = (([Drug]_0 - [Drug]_f)/[Drug]_0) \times 100$$

Example 5

Release Kinetics of Natural Active Ingredients from the Nanoparticles

The in vitro release kinetics of the nanoparticles will be evaluated in phosphate buffered saline (PBS) and fetal bovine serum (FBS). A defined amount of primary/secondary ingredients encapsulated in nanoparticles will be suspended in 10 ml of PBS, and the solution will be kept at room temperature. At various time intervals, the solution will be vortexed, and an aliquot (1 mL) of the solution removed and subjected to centrifugation at 13,000 rpm to separate released active ingredients from nanoparticle-encapsulated material. The concentration of released drug will be determined by and HPLC or LC/MS/MS. The percent release of encapsulated ingredients will be determined according to the following formula:

$$\% \text{ Release} = ([Drug]_{f,t})/([Drug]_0) \times 100$$

where $[Drug]_{f,t}$ is the concentration of primary and secondary active ingredients in the supernatant at time t. Similarly, to determine the release kinetics in FBS, a defined amount of primary and secondary active ingredients encapsulated in nanoparticles will be suspended in 10 ml of 20% FBS. Release kinetics will be analyzed as described for PBS.

Example 6

Analysis of Particle Size by DLS and TEM

Size distribution of primary and secondary active ingredients-encapsulated nanoparticles in an aqueous dispersion will be determined using a Malvern zeta sizer (Malvern Instrumentation Co, Westborough, Mass., USA). The size and morphology of the nanoparticles will also be examined using a JEOL JEM-100CX transmission electron microscope.

Example 7

Lycopene and Bone Health

Work of the inventors of the present invention, both experimental work and work with humans, provides evidence for a positive effect of the potent antioxidant "Lycopene" on bone health. Postmenopausal women with low dietary intake of lycopene (based on dietary history food frequency questionnaire) exhibited lower serum lycopene values compared to corresponding postmenopausal women with high dietary intake of lycopene. Women with higher serum lycopene exhibited reduced oxidative stress (as indicated by decreases in lipid and protein oxidation, increases in the enzymatic activities of catalase an superoxide dismutase) that was associated with improve bone resorption markers (u-NTX, s-CTX) and bone formation markers (s-Osteocalcin and bone-specific ALP).

Example 8

Lycopene Plus Other Antioxidants and Bone Health

Supplementation of healthy postmenopausal women with 30 mg/day of lycopene for 6 months significantly improved oxidative stress and bone turnover markers: significant decreases in u-NTX and s-CTX and increases in s-OC and s-BALP. The benefit of Lycopene on bone turnover rate and bone health was further enhanced when combined with green tea extract and/or pomegranate extract.

In one embodiment, the composition of the present invention comprises active ingredients, wherein the active ingredients comprise *Lepidium Sativum* or other *Lepidium* extracts, calcium, vitamin D2/D3 and antioxidants.

In one embodiment, the active ingredients further comprise additional ingredients. The selected from the group consisting of flavonoids or isoflavones, bromelain and magnesium, manganese, and combinations thereof. In one embodiment, the calcium/magnesium ratio is 2/1.

In one embodiment, the composition further comprises nanoparticles, wherein the active ingredients are encapsulated within each nanoparticle.

In one embodiment, the nanoparticles are selected from the group consisting of chitosan nanoparticles, poly(lactic-co-glycolic acid) (PLGA) nanoparticles, chitosan cross linked to fatty/bile acids nanoparticles, alginate-chitosan nanoparticles, hybrid crosslinked polyvinylpyrrolidone (PVP) hydrogel nanoparticles, chitosan grafted PLGA nanoparticles, and combinations thereof.

The present invention provides a method for treating a bone condition of an animal, wherein the method comprises: treating the bone condition of the animal, said treating comprising introducing the composition of the present invention into the animal.

In one embodiment, the animal is a human being.

In one embodiment, the animal is a non-human species of animal.

In one embodiment, the bone condition being treated is osteoporosis.

In one embodiment, the bone condition being treated is a bone fracture.

In one embodiment, said introducing the composition comprises introducing the composition into the animal via a delivery selected from the group consisting of an oral delivery, a topical delivery, an injectable delivery, a toothpaste delivery, and combinations thereof.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A composition, comprising:
 a nanoformulation of active ingredients encapsulated within nanoparticles, wherein the active ingredients comprise *Lepidium Sativum*, calcium, vitamin D, and at least one antioxidant.

2. The composition of claim 1, wherein the active ingredients further comprise magnesium, and wherein the ratio of calcium to magnesium is 2/1.

3. The composition of claim 1, wherein the active ingredients further comprise manganese.

4. The composition of claim 1, wherein the at least one antioxidant comprises flavonoids, isoflavones, lycopene, green tea extract, pomegranate extract, or combinations thereof.

5. The composition of claim 4, wherein the at least one antioxidant comprises flavonoids.

6. The composition of claim 4, wherein the at least one antioxidant comprises the isoflavones.

7. The composition of claim 4, wherein the at least one antioxidant comprises lycopene.

8. The composition of claim 4, wherein the at least one antioxidant comprises green tea extract.

9. The composition of claim 4, wherein the at least one antioxidant comprises pomegranate extract.

10. The composition of claim 1, wherein the nanoparticles comprise chitosan nanoparticles, poly(lactic-co-glycolic acid) (PLGA) nanoparticles, chitosan cross linked to fatty acids nanoparticles, chitosan cross linked to bile acids nanoparticles, alginate-chitosan nanoparticles, hybrid crosslinked polyvinylpyrrolidone (PVP) hydrogel nanoparticles, chitosan grafted PLGA nanoparticles, or combinations thereof.

11. The composition of claim 10, wherein the nanoparticles comprise the chitosan cross linked to fatty acids nanoparticles.

12. The composition of claim 10, wherein the nanoparticles comprise the chitosan cross linked to bile acids nanoparticles.

13. The composition of claim 10, wherein the nanoparticles comprise the alginate-chitosan nanoparticles.

14. The composition of claim 10, wherein the nanoparticles comprise the hybrid crosslinked PVP hydrogel nanoparticles.

15. The composition of claim 10, wherein the nanoparticles comprise the chitosan grafted PLGA nanoparticles.

16. A method of forming the composition of claim 1, comprising encapsulating the active ingredients within the nanoparticles.

17. A method for treating a bone condition of an animal, said method comprising:
 treating the bone condition of the animal, said treating comprising introducing a therapeutically effective amount of the composition of claim 1 into the animal.

18. The method of claim 17, wherein the animal is a human being.

19. The method of claim 17, wherein the animal is a non-human species of animal.

20. The method of claim 17, wherein the bone condition being treated is osteoporosis.

21. The method of claim 17, wherein the bone condition being treated is a bone fracture.

22. The method of claim 17, wherein said introducing the composition comprises introducing the composition into the animal via a delivery selected from the group consisting of an oral delivery, a topical delivery, an injectable delivery, a toothpaste delivery, and combinations thereof.

* * * * *

UNITED STATES PATENT AND TRADEMARK OFFICE
CERTIFICATE OF CORRECTION

| | | |
|---|---|---|
| PATENT NO. | : 8,563,053 B2 | Page 1 of 1 |
| APPLICATION NO. | : 12/912826 | |
| DATED | : October 22, 2013 | |
| INVENTOR(S) | : Shaker A. Mousa | |

It is certified that error appears in the above-identified patent and that said Letters Patent is hereby corrected as shown below:

In the Specification

COLUMN 4

Line 37, after "under" delete "stiffing" and insert --stirring--

COLUMN 5

Line 48, after "with" delete "stiffing" and insert --stirring--

Signed and Sealed this
Eighteenth Day of February, 2014

Michelle K. Lee
*Deputy Director of the United States Patent and Trademark Office*